United States Patent [19]

Graupe

[11] 4,030,141
[45] June 21, 1977

[54] MULTI-FUNCTION CONTROL SYSTEM FOR AN ARTIFICIAL UPPER-EXTREMITY PROSTHESIS FOR ABOVE-ELBOW AMPUTEES

[75] Inventor: Daniel Graupe, Fort Collins, Colo.

[73] Assignee: The United States of America as represented by the Veterans Administration, Washington, D.C.

[22] Filed: Feb. 9, 1976

[21] Appl. No.: 656,412

[52] U.S. Cl. .................................................. 3/1.1
[51] Int. Cl.² ...................... A61F 1/00; A61F 1/06
[58] Field of Search .......................... 3/1.1, 12–12.7

[56] References Cited

UNITED STATES PATENTS

| | | | |
|---|---|---|---|
| 3,491,378 | 1/1970 | Ioffe et al. | 3/1.1 |
| 3,735,425 | 5/1973 | Hoshall et al. | 3/1.1 |

OTHER PUBLICATIONS

"Statistical Analysis of Myoelectric Potentials in Man" by G. W. Lange et al., The Basic Problems of Prehension, Movement, and Control of Artificial Limbs, Proceeding the Institution of Mechanical Engineers, vol. 183, Part 3J, 1968–1969, pp. 135–140.
"A Study of Myo–Electric Signals for Arm Prosthesis Control" by D. Bousso et al., Bio–Medical Engineering, vol. 6, No. 11, Nov. 1971, pp. 509–516.

Primary Examiner—Ronald L. Frinks
Attorney, Agent, or Firm—Edwin L. Spangler, Jr.

[57] ABSTRACT

This invention relates to an improved EMG-based method for actuating a prosthetic appliance wherein a single pair of electrodes may be used to actuate several artificial limb movements by way of sampling and repeatedly resampling substantially the entire time function of the myoelectric signal as it appears on the limb stump over a period so short that the signal remains quasi-stationary, comparing a minimum number of parameters of such signals with a range of values of these same parameters stored within the data bank of a microcomputer, and actuating one or more functions of a prosthetic appliance whenever the current data for the sampled parameters all falls within a preselected domain chosen on the basis of the historical data. This invention also encompasses the apparatus for using the EMG signals developed by the patient in the stump for controlling the movements of a prosthetic appliance which comprise means connected to process the EMG signals so as to differentiate between the various functions to be performed thereby based upon a minimum number of parameters of said signals, means for storing historical data concerning the range of values said parameters vary over for each function, means for repeatedly sampling current data on said parameters and comparing same with the stored data during a brief time interval, and means operative to initiate one or more functions whenever the current data on the chosen parameters falls within an arbitrary domain chosen on the basis of said historical data.

31 Claims, 2 Drawing Figures

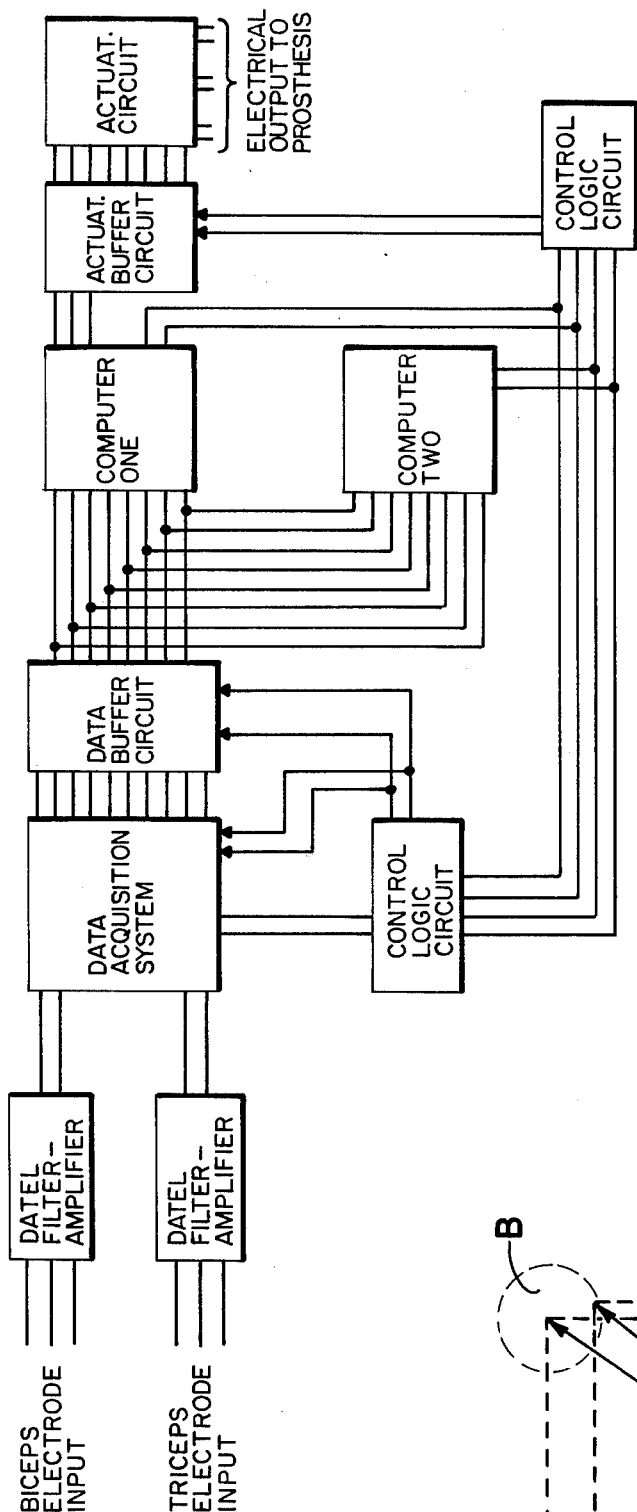
Fig_2
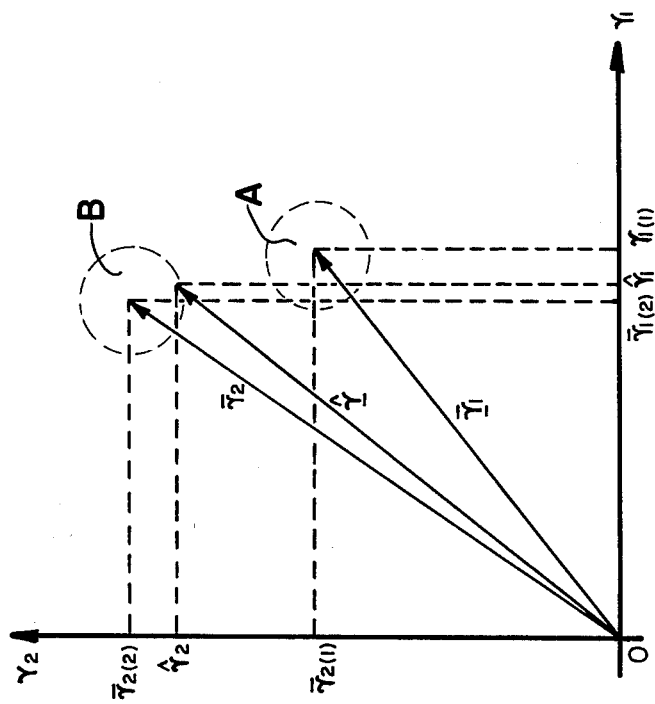
Fig_1

MULTI-FUNCTION CONTROL SYSTEM FOR AN ARTIFICIAL UPPER-EXTREMITY PROSTHESIS FOR ABOVE-ELBOW AMPUTEES

The development of prosthetic aids for amputees, especially upper-extremity amputees, is not a simple task because much more must be designed into a prosthesis than the functional necessities of the patient. For instance, many well engineered prostheses have been rejected, not because they failed electrically or mechanically, but because they failed to consider the human reaction to the prosthesis. Prostheses that make the amputee conspicuous, are embarrassing or draw unnecessary attention to his or her infirmity will ultimately be rejected for the simple reason that they become reluctant to use a prosthesis that makes them feel self-conscious. Another reason amputees often reject certain prosthetic appliances is their weight and size or volume. Some others are objected to because they are incapable of performing many of the missing limb functions. The latter objection is especially significant to above-elbow amputees where the several major limb functions of elbow and wrist movement as well as grasp have been lost. Still other prostheses are rejected by the patient because, while they perform the missing limb functions, they do so at the expense of a complex and often heavy apparatus that entails the use of many sets of electrodes. Obviously, if a patient has no other choice, he or she will use whatever prosthesis is available in order to perform routine tasks; however, it would be far better if one were able to construct a prosthesis that would be both asethetically as well as functionally pleasing to the patient.

From a technological standpoint, it is impossible to design a prosthetic device that can replace the human arm, or any other limb for that matter in terms of performance at the user's will. The human arm especially, is too complex to be duplicated artifically at the present time. Any upper-extremity prosthesis, therefore, will automatically fail to satisfy fully any patient's desires because the patient would naturally desire a flesh and blood duplicate of the limb he or she has lost. Since we cannot satisfy a patient's specific needs, then the primary concern must be with the patient's more general needs and one must try to design a prosthesis that can satisfy these demands. The basic requirements of any artificial arm are, of course, elbow bending, elbow extension, wrist pronation, wrist supination, hand grasping and hand opening. Such an arm would have three degrees of freedom. In addition to these functional requirements, an artificial arm must be cosmetically appealing and silent in operation. While there are many other desirable qualities such as, for example, sensory feedback they are of secondary concern when compared with the more basic requirements mentioned above.

Also, any artificial arm has to be "fixed" to the patient so that he has willful control of the device. Thus, there must be a coordinating of the patient's will and the performance of the prosthesis. Furthermore, this control must be as easy and as simple as possible and must result in a smooth natural motion. The simpler the control becomes the easier the patient training will be. The need for extensive training in the operation of a prosthesis will result in its being poorly accepted. What's more, one must also consider the wide range of intelligence of the patients who will be using the device because many patients have also undergone emotional and psychological stress as the result of losing their limb and, therefore, it may be hard for these patients to give any prosthesis, no matter how good, a reasonable and objective trial period. Accordingly, it is obvious that no prosthesis will be able to satisfy all the patients even if all patients are capable of using it but, nonetheless these are the goals one wishes to attain.

Apart from the emotional aspects outlined above, an artificial limb should be adaptable if it is to answer the needs of amputee patients. Certain patients, for instance, may like an artificial arm that can have interchangeable parts, such as a powered hand or hook, depending on their needs at any given moment. A successful prosthesis must also be relatively light in weight and compact because one that is cumbersome will not be tolerated by an amputee. Along the same line, a prosthesis that can be built in modules will allow a clinical engineer to assemble and adjust the prosthesis to the comfort and particular disability of the patient. Some patients, for example, due to the nature of their disability will have a small stump so that parts of a modular prosthesis can be inserted into the hollow humeral section of the prosthesis when it is fitted to the stump while others cannot. In other words, it is a decided advantage if a prosthesis can be designed so that it can be personalized to satisfy the requirements of each patient. Last but by no means least is the paramount requirement of an artificial limb that it be reliable so that the amputee can have complete confidence that his or her artificial limb will operate consistently and without actuation errors.

In the past, simple artificial limb functions have, for the most part, been initiated by some movement of another part of the patient's body suffering from no motor disfunction such as, for example, using shoulder or stomach movements to initiate elbow bending, wrist movements or grasp. While the patient's brain initiated the muscle movement which, through the medium of harness switches and the like, eventually brought about the desired elemental movement of the prosthesis, it was an indirect one (unsynchronized) as opposed to direct synchronous control over those muscles, or what's left of them, that were originally responsible for bringing about the required response and near simultaneous control over the prosthesis by using his or her brain to actuate the same muscle system that he or she formerly used to control the limb that is now missing. While this is, and always has been, a noteworthy objective, the past attempts at implementing what is now commonly known as an "EMG - Actuated System" for controlling artificial limbs has met with only limited success and then only to control one, or at most two, very basic functions such as, for example, lower limb movements which are far less complex and, therefore, easier to replace than upper limb movements. Until now, there has been no successful EMG-actuated prosthesis for upper arm amputees. Especially in the case of an amputated arm, it makes a great deal of difference just what functions remain intact. For instance, a below-elbow arm amputee in all probability still has the ability to bend and straighten his or her arm and, quite often, control over the wrist movements as well; whereas, the above-elbow amputee must be provided with all of the following arm functions, namely:

1. elbow bending
2. elbow extension
3. wrist pronation 4. wrist supination
5. grasp opening
6. grasp closing Many of the problems associated with the use of myoelectric signals (also commonly known as "electromyographic" or EMG signals) to actuate a prothesis are traceable to the manner in which the prior art researchers interpreted the signal itself. Without going into detail at this point, it is sufficient to note that their analysis of it was, and still is, such that at least as many electrode locations were required on the patient as there were functions that the prosthesis was called upon to perform. With this being the case, the immediate problem becomes a physical one in finding sufficient space on the stump of the lost limb for attaching the several electrodes required to perform more than the most elementary functions. The stump of a lost leg, for example, presents a substantial area for electrode attachment while the necessary functions to be performed by the prosthesis are more or less rudimentary when compared with the more complex systems of the human arm. Even some of the below-elbow arm functions can be handled adequately by the existing EMG-controlled prostheses. When, however, one attempts to re-establish the multiple-function capabilities of the human arm amputated above the elbow, the prior art EMG-controlled artificial limbs become totally inadequte as anywhere from a minimum of about eight separate electrode locations are needed up to twelve or more to take care of the complex movements and the available area on the stump of the upper arm is just not big enough to accommodate all these electrode locations. While there need not necessarily be the same number of electrode locations as there are limb functions to be performed, the existing EMG-controlled prostheses still require several such locations for a very few functions. The physical problem of having enough space available could, conceivably, be solved, however, there are others that do not admit to any simple solution.

Not the least of these other problems is the one of unwanted interactions between closely-placed electrodes. These interactions which do occur under certain circumstances not infrequently lead to the prothesis performing the wrong functions and, obviously, such unreliability cannot be tolerated. As previously noted, a patient who has lost a limb is already in a traumatized state and anything like a prothesis that not only fails to function in the manner he or she wills it, but performs in a way that is contrary to the patient's will, is totally unsatisfactory no matter how cleverly it is designed.

Completely apart from the interaction between closely-spaced electrodes is the problem of unreliability resulting from too many of them. Obviously, it is a good deal easier to keep three or four electrodes in proper contact with the surface of the stump from which the EMG signals are tapped than it is a dozen. It should be noted that the preferred electrode is the so-called "surface electrode" which is glued to the skin or held in contact therewith by a bandage. By way of contrast, the internal type of electrode necessitates the skin being punctured and repunctured periodically because, as new tissue grows around the resulting wound, it leads to deterioation if not eventual loss of the desired electrical contact.

From the foregoing, it becomes rather apparent that the ideal EMG-controlled system would involve a minimum number of electrodes. Looking at it another way, the thing that is needed, especially by above-elbow amputees where the stump area is small yet the functions to be performed are numerous, are electrodes capable of controlling more than one function.

The prior art attempts to accomplish this noteworthy objective have, however, met with little success. The primary reason for this is that the early investigators used only a portion of the information the EMG signal contained, specifically, the low frequency portion and, as a result, more electrodes were needed to supply the inputs required to control the various functions that had to be furnished to the patient. Contrary to the above approach of using a plurality of electrodes and only part of the information available from the EMG signal, it has now been found in accordance with the teaching of the instant invention that the better approach is one of using the fewest possible number of electrodes while, at the same time, making beneficial use of virtually all the information that is contained in the signal. Applicant was, in all probability, the first one to recognize the fact that tapping the EMG signal for all the information it contains and using this to cut down on the number of electrodes needed to accomplish a given set of functions was the solution to the many problems previous investigators had experienced with EMG-actuated prostheses. Whether he was or not is immaterial because, the fact of the matter is, no one before applicant found a practical way to utilize all the information the signal has to offer. Accordingly, it is applicant's method and apparatus for analyzing the signal and putting the information gained from such an analysis to practical use that constitutes the true novelty in his contribution. This is no simple task and, in fact, other investigators have tried to do it without success. To appreciate why the prior art attempts to analyze and utilize the full potential of the EMG signal have met with failure, one needs to understand the nature of the signal itself.

The EMG signal as recorded at a surface electrode is the outcome of firing of between approximately 50 and 500 motor units at intervals which, for a large number of units, can be observed as occurring at random intervals. In fact, the intervals can be shown to be nearly statistically independent, i.e., completely random, and distributed in a Poisson-process fashion. The surface-recorded EMG, however, receives these signals after they pass through muscle tissue that acts as a filter which one can consider to be very close to a linear filter (see Brody et al, Med. & Biol. Eng. pp. 29–41, January, 1972). Accordingly, the EMG signal as recorded by the surface electrode is a stochastic signal which, when its voltage of a few millivolts is plotted against time, has the form of a noise signal that might have been produced by some instrument noise. Furthermore, for a sufficiently large number (N) of motor units whose firing is recorded at one electrode location (in fact, for $N>200$), the recorded signal can be proven to be approximately Gaussian (see Papoulis "Probability, Random Variables and Stochastic Processes," McGraw Hill, New York, 1965, pp. 559–575). This Gaussian feature is of importance as will appear presently.

Thus, while it is easy to recognize the importance of squeezing all or nearly all the information contained in the EMG signal, to do so would appear to require the processing of a near-infinite number of features of the pattern, i.e., to process features at every frequency from almost d.c. to some 5000 Hz. This is certainly a very lengthy task requiring lots of computational hardware and, of course, the amputee cannot carry a large computer and, even if this were possible, it would be manifestly impractical to wait for it to complete its analysis of the signal before initiating the desired function willed by the amputee.

It is for these and other reasons that the early investigators abandoned their attempts to directly analyze all the many elements of the pattern of the EMG signal as it appears at the electrodes in favor of the more manageable approach of looking only at the lower frequencies at the cost of having to increase the number of electrodes in order to obtain the needed information. Applicant, however, was unwilling to accept the fact that all or nearly all the information available in this pattern of the EMG signal which was already recognized to be a stochastic time series could not be reduced to a minimum number of workable parameters. Accordingly, he proceeded to develop a mathematical model of the EMG signal, identified its parameters, selected certain of those parameters which were readily ascertainable in a realistic time frame and proceeded to determine if these chosen parameters allowed him to differentiate between two or more different limb functions, all from the EMG information gathered by a single pair of surface electrodes. Notwithstanding the teaching of the prior art to the contrary, applicant did, in fact, find that there were only a few parameters (three to eight per limb function) that needed to be looked at instead of ten to hundreds of times this many and that by comparing them with a similar set of parameters obtained for other limb functions and with other known data, sufficient discrete information can be obtained from the EMG signal accessed by a single electrode pair to control more than one, actually several, limb functions. He was also the first in the art to add the time parameter to analysis of the EMG signals in a way that the signal was analyzed repeatedly each fraction of a second and compared with its own past history. Without this reduction of the EMG signal pattern to a set of a very few parameters effective to discriminate among the several limb functions, it would have been impossible with a patient-borne control system to accomplish smooth flowing prosthesis movement essentially synchronized with the mental act of the amputee.

More specifically, applicant analyzed the EMG signal in accordance with a mathematical model thereof and determined that a near minimum number of no more than eight of its parameters need be examined and compared in order to differentiate between several different limb functions and, what's more, these parameters were all available from a single EMG recording obtained at a single electrode location. Applicant even found upon comparing the more complex Autoregressive Moving average (ARMA) mathematical model of the EMG signal with its simpler Autoregressive (AR) counterpart that, unexpectedly classification was achieved without having to greatly increase the number of parameters, i.e., it remained possible to differentiate between the several limb-controlling functions without going beyond three, or at the most eight, such parameters. Moreover, while these parameters of the EMG signal change with the passage of time, applicant has discovered that by examining the signal within a short discrete time interval closely related to the elapsed time within which the patient's mind initiates a given function and the prosthesis responds to carry it out, the signal is stationary enough for all practical purposes such that the change that would otherwise take place in the parameters if sampled over a longer time interval becomes insignificant.

It is, therefore, the principal object of the present invention to provide a novel and improved EMG-controlled system for actuating artifical limbs.

A second objective is the provision of a system of the type aforementioned which is ideally suited for use in multi-function applications having minimal stump area available for attachment of the surface electrodes.

Another object of the invention herein disclosed and claimed is to provide prosthesis control apparatus that is capable of controlling as many as six different functions from a single set of surface electrodes.

Still another objective is the provision of an EMG-controlled system which, for the first time, provides the upper arm amputee with the means for controlling elbow and wrist movements as well as grasp while keeping the control circuitry and associated hardware to a minimum.

An additional object is to provide a method and apparatus for using an EMG signal or signals to control a prosthesis that is ideally suited for use with above-elbow bilateral amputees who have no other arm or hand movement available to them.

Further objects of the within described invention are to provide a prosthesis control which is simple, lightweight, efficient, dependable, fast, compact, versatile and aesthetically acceptable to the amputee.

Other objects will be in part apparent and in part pointed out specifically hereinafter in connection with the description of the drawings that follows, and in which:

FIG. 1 is vector diagram illustrating a representative dual function discrimination scheme; and, FIG. 2 is a block diagram showing the control circuitry for taking two myoelectric signals, one from the biceps and one from the triceps of an above-elbow amputee, processing it and using the resultant six outputs which are capable of controlling elbow bending, wrist rotation and grasp.

Knowing that the EMG singal as it appears at a surface electrode constituted a stochastic time series, appplicant realized that it could be uniquely modeled by an Autoregressive Moving Average (ARMA) model having the following form:

$$y_k = a_1 y_{k-1} + a_2 y_{k-2} + \ldots a_n y_{k-n} + w_k + b_1 w_{k-1} + b_m w_{k-m} \quad \text{(Eq. 1)}$$

where $k = 0, 1, 2, \ldots$ and denotes the sampling interval, i.e., the discrete time interval; $y_k$ is the recorded signal or EMG in our case; and $w_k$ is white noise that is not susceptible to being measured but which can be rigorously calculated in terms of an approximation that converges to the true but unknown $w_k$ which, from the point of view of the stochastic process is essential to the description of the ARMA process $y_k$ above. Also, $a_i$ and $b_j$ are the autoregressive (AR) and the moving average (MA) parameters respectively where $i = 1 \ldots n$ and $j = 1 \ldots m$. Now, the number which represents the sum of AR and MA parameters $(n + m)$ is a finite minimum number of parameters needed to characterize the ARMA process — in our case the EMG signal.

Accordingly, the problem becomes one of not only identifying the foregoing ARMA parameters but, once this has been done, differentiating between the several limb functions using only $n + m$ parameters of a single EMG recording. This EMG signal found at a given electrode location is made up of the firing of many different motor units. Fortunately, while many of the same motor units may fire and cooperate to produce the EMG signal seen at a particular electrode location, enough different motor units, motor-unit firing rates and different muscle fibers are involved in the performance of the various functions to enable us to differentiate therebetween. Saying this another way, each particular function calls into play a certain set of motor units, specific firing rates for the latter and different muscles, therefore, while some of the same motor units, firing rates and muscles will be used in the performance of other and different functions, it will not be the same combination of them used in the performance of both functions. Some 2600 recordings, for example, all demonstrated a difference in the value of the $n+m$ parameters.

If all the statistical information contained in the EMG signal is to be used, the term $w_i$ in Equation (1) must be statistically independent. $w_k$, on the other hand, is not usually statistically independent, but rather, is only "white noise", that is, completely uncorrelated. It can be shown, however, that if $y_k$ in Equation (1) is Gaussian, then $w_k$ becomes, in fact, statistically independent. Furthermore, it is known that $y_k$ does becomes very nearly Gaussian if many motor units are involved. Many motor units are involved at both the biceps and triceps, therefore, by placing the electrodes at these locations, $y_k$ becomes nearly Gaussian and $w_k$ nearly statistically independent. Thus, at least when using the biceps and triceps as electrode locations, the near Gaussian approach appears valid and worthy of being explored further. Later on, it will be shown that, contrary to what one would expect, even in the non-Gaussian case where relatively few motor units are involved and one would expect to need a non-linear mathematical model which is very complex and beyond the scope of a patient-borne prosthesis to cope with due to its inherent inability to perform the necessary function discrimination analysis within the time frame of near-simultaneous action synchronized with the mental act of the amputee, this is actually not the case and a linear model can, in fact, be used for adequate discrimination between limb functions. Actually, the model of Equation (1) above and its parameters are still unique for non-Gaussian $y_k$ (see J. L. Doob: Stochastic Processes, John Wiley & Sons, NYC, 1953 on this point). Be that as it may, for the present the near-Gaussian case will be explored to a conclusion.

Having overcome the first major problem, namely, that of squeezing out nearly all the information the EMG signal has to offer using a manageable, indeed minimal, number of electrodes where both the near-Gaussian properties of the signal helped as did the property inherent in a surface electrode of receiving a signal made up of the firing of a large number of nerve motor units, other significant problems still remain. Not the least of these problems is the fact that the EMG signal is not stationary, i.e., its parameters change with time, whereas, Equation (1) calls for the identification of stationary parameters $a_1$, $b_i$. Once again, unexpectedly, this problem disappears in practice because when using the EMG signal to actuate a prosthetic appliance, it must do so substantially instantaneously so that the limb will react simultaneously with the patient command and, when such a time parameter is imposed upon our near-Gaussian mathematical model, the signal becomes substantially stationary. In other words when, for all practical purposes, we must complete identification of the EMG signal picked up by the electrodes in, say 0.2 seconds or thereabouts, the signal is quasi-stationary because while its parameters still change a little with time, they do so to such a slight extent that they have no recognizable effect upon the all important classification function. It becomes possible, therefore, to perform identification of a model as in Equation (1).

The algorithm necessary to perform the desired identification could be anyone of many which are known to converge; however, the wise choice is one that converges as fast as possible, i.e., needs the smallest number of data points to establish $y_k$. Furthermore, the chosen algorithm should demand a minimum amount of computation during each sampling interval. Fortunately, a least squares identification algorithm is known to possess the fastest convergence features for a linear model. In fact, the least squares algorithm is so effective that complete function recognition and control was achieved with real hardware in just 0.8 seconds without the use of hardware multipliers to perform multiplication and divisions. Obviously, as the speed of microprocessors increases and computation time is shortened through the use of hardward multipliers already available, the least squares algorithm will be entirely adequate to provide the necessary function recognition as well as control thereof nearly simultaneously with the mental act of the patient initiating same. Actually, when applicant got the sampling interval down to 0.2 seconds, one patient complained of it being too fast.

Another alternative algorithm is the so-called "sequential learning algorithm" which has the advantage over the least squares algorithm of a faster inter-interval computational time. Either the least squares or the sequential learning algorithms or speeded-up versions of them will function nicely in the instant prostheses control system and there well may be others that will also do an adequate job provided, of course, that they answer the two requirements of rapid convergence and near minimal computation time. These algorithms form no part of applicant's invention per se and complete details concerning both the least squares and sequential learning ones can be found in chapters 6 and 7 of applicant's book entitled: "Identification of Systems", Van-Nostrand Reinhold, N.Y., 1972. In fact, any other identification algorithm can be used so long as it converges, additional examples of such convergent algorithms being found in chapters 8, 9 and 12 of applicant's book aforementioned.

Now, what has been said above applies to those essentially Gaussian signals derived from many motor units firing simultaneously such as are picked up by surface electrodes located at the triceps or biceps. There remains the question of the non-Gaussian signal picked up by a needle electrode or even a surface electrode positioned where it picks up only the firing of a small number of motor units. In such a situation, one would need a non-linear model to $y_k$, however, this model usually requires "a priori" knowledge of the signal which, unfortunately, is not available in the EMG case nor can it be derived in any consistent manner. Furthermore, its identification is quite complex, requires lengthy computations and cannot be performed within the constraints on both speed and the amount of computational hardware that exist for an amputee-borne prosthesis. Accordingly, the non-linear approach to the non-Gaussian signal becomes completely unrealistic.

Unexpectedly, however, applicant discovered that the variance between the linear model of Equation (1) and the actual EMG signal resulted in an error which was no greater than that obtained via a non-linear model in which no"a priori" assumptions were made, but instead, a zero-memory non-linearity cascaded by a linear filter was assumed. Such a model is the best that one can hope to get as applicant points out in his book identified previously. Moreover, since it is this variance in the model error that provides us with an indication of the quality of the model, i.e., the greater the error the worse the model, remarkably there appears to be no justification whatsoever for using the non-linear approach for the analysis of the non-Gaussian EMG signals even if it were possible to do so within the time frame allowed and the constraints of the hardware that the amputee can reasonably be expected to carry. If this were not sufficient justification in itself, the linear model is also, even in the non-Gaussian case, unique and linearly-optimal while at the same time providing the information necessary to discriminate among the various limb functions. The latter is of course, all one really cares about in the long run. It is the linear approach, therefore, in both the near-Gaussian situation and the non-Gaussian one that is the simplest to compute, involves the fewest number of parameters to discriminate between limb functions, is fast, and results in one being able to squeeze nearly all the significant information out of the EMG signal in the first two statistical moments under the worst possible circumstances and essentially all moments in the best ones. It should, perhaps, be pointed out that whether $y_k$ is nearly Gaussian or, alternatively, non-Gaussin is significant insofar as the choice of a particular identification algorithm is concerned. Again, the least squares algorithm is known to be fastest in convergence (see: G. Saridis, Proc. I.E.E.E. Decision and Control Conf., New Orleans, 1972); whereas, the sequential learning algorithm has the advantage of being faster in computation time per sampling interval.

Now, while the ARMA model of Equation (1) solves the problem, it is computationally slower than we would like if the time lapse between the mental act of the amputee and its operational response in the apparatus is to be kept at a minimum, say 0.2 seconds or thereabouts. There is a considerably simpler pure autoregressive (AR) model that has the advantage of a very much shorter computation time for identifying its parameters but, unfortunately, at the expense of usually requiring more than the (n + m) parameters of the ARMA model to discriminate among the several limb functions. This AR model is actually a first stage in the derivation of the more complex ARMA model and is represented as follows:

$$y_k = \gamma_1 y_{k-1} + \gamma_p y_{k-p} + w_k \quad \text{(Eq. 2)}$$

where $\gamma_i$ are the AR parameters. Otherwise, the various terms of Equation (2) have the same meanins as in EQUATION (1). Unexpectedly, applicant has determined that while the parameters (p) of Equation (2) exceed the parameters (n + m) of Equation (1), classification can, in fact, be obtained where p = 3 or 4. This means, obviously, that there is absolutely no necessity for using the ARMA model when all we need is obtainable much faster and more simply from the AR model using three, or at most eight, parameters which is still a very low number when compared with the prior art EMG-controlled prosthese which required from ten to hundreds of times this many or, alternatively, from four to 12 times as many electrode locations to control the same number of limb functions. Hence, it is only necessary to identify $\gamma_i$ of Equation (2) and we can forget about $a_i$ and $b_i$ of Equation (1). In so doing, however, the same theory and methods of justification outlined previously still apply because Equations (1) and (2) are but different versions of the same model.

Having established that even with the simple AR model of Equation (2) we can, in fact, discretely identify a given limb function using no more than four parameters, the task then become one of implementing the theory thus developed. This has been accomplished in a unique manner, namely, by identifying a specific periodically updated set of historical parameters $\gamma_1$, $\gamma_2$ and $\gamma_3$ or up to $\gamma_1 .. \gamma_8$ for a particular amputee; storing those historical parameters in the memory of a microcomputer; comparing the stored set or derivative thereof with an instantaneously developed current set; and, actuating or holding a particular function depending upon the outcome of the comparison. A better understanding of this procedure can best be had by referring to the diagram of FIG. 1 wherein a simplified system using only two parameters and two functions has been represented. Even though, as previously noted, the actual number of parameters (p) considered is three or even up to eight, a two-dimensional graphical representative of a three-dimensional system becomes complex and confusing, whereas, the two-dimensional one is not. Moreover, anyone of ordinary skill can, of course, extrapolate the teaching of the two parameter system into one having three up to as many as eight parameters very easily.

In the diagram, the predetermined values for parameters $\gamma_1$ necessary to actuate function (1) or function (2) are plotted along the X-axis. The specific parameter which must be present before function (1) will be initiated is identified as $\gamma_{1(1)}$. Similarly, $\gamma_{1(2)}$ is the same parameter with a different numerical value necessary to actuate function (2). Likewise, $\gamma_{2(1)}$ and $\gamma_{2(2)}$ are the second parameter $\gamma_2$ with predetermined values plotted along the Y-axis corresponding to function (2). For purposes of illustration, function (1) will be assumed to be the one that controls elbow bending and function (2) wrist pronation as follows:

$\gamma_{1(1)} = \gamma_1$ for function (1), say, elbow bending
$\gamma_{2(1)} = \gamma_2$ for function (1), say, elbow bending
$\gamma_{1(2)} = \gamma_1$ for function (2), say wrist pronation
$\gamma_{2(2)} = \gamma_2$ for function (2), say wrist pronation
$\gamma_i(\nu) = $ reference $\gamma_i$ for function $\nu$ $$\gamma_{(i)} = \begin{bmatrix} \gamma_{1(i)} \\ \gamma_{2(i)} \end{bmatrix} = \text{vector of dimension } p = 2$$

The dark areas in the diagram labeled "A" and "B" denote the recognition areas or domains for functions (1) and (2) respectively. More specifically, during the calibration identification runs performed on the amputee, a series of different values are obtained for each parameter that is going to be evaluated to determine whether a given function is to be initiated or not. These maximum and minimum values, $\gamma_{i(v)}$ max. and $\gamma_{i(v)}$ min., define the range over which such parameter varies in the individual patient for a given function, say, elbow bending. Therefore, these values are incoded into the memory of the microcomputer and used for comparision purposes when the instantaneous EMG signal generated by the patient includes such a parameter. If the identified parameter (vector) $\bar{y}_1$ in FIG. 1 terminates within recognition area "A" as shown, then the preselected conditions for actuating the elbow bending function are satisifed and an appropriate output will be sent to that portion of the prosthetic appliance responsible for bending it at the elbow joint say, for example, the so-called "VAPC elbow" or its equivalent. Vector $\bar{y}_1$ is, of course, determined by parameters $\gamma_{1(1)}$ and $\gamma_{2(1)}$ which defines the terminus of the vector. In a similar fashion, parameters $\gamma_{1(2)}$ establish the magnitude and direction of vector $\bar{y}_2$ which if it terminates inside area B thus satisfying the conditions set up for initiation of the wrist pronation function (2). Of course, had the values of either the $\gamma_1$ or the $\gamma_2$ parameters been such that vectors $\bar{y}_1$ or $\bar{y}_2$ fell outside areas A or B, then the prosthesis would be kept in a "hold" state so as to not actuate.

Finally in FIG. 1, vector $\hat{\gamma}$ terminating at the edge of area B represents one of many minimum conditions necessary before actuation of the wrist pronation function will proceed. Its point of termination is defined by $\hat{\gamma}_1$ and $\hat{\gamma}_2$ as before. Areas A and B are selected such that all the real values $\gamma_{i(v)}$ taken during periodic testing of the patient under various conditions fall inside thereof, otherwise, he or she might, under certain circumstances, be unable to initiate a particular function at will. On the other hand, the area chosen should also be limited in extent such that combinations of parameters whose values fall outside the range thereof taken during the calibration phase do not trigger a function contrary to the will of the patient.

Obviously, the simplst classification takes place using rectangular areas for A and B in the case of two parameters and boxes or hyperboxes when $p>2$. More complex, but nevertheless improved, recognition occurs when the recognition areas A and B are elliptical or hyperelliptical. This is simply done by employing the standard deviation $\sigma$ or some function thereof for each $\gamma_{i(v)}$.

Applicant has thus discovered a unique method for controlling the movements of a prosthetic appliance, even those complex ones having three degrees of freedom, which consists of using a very few surface electrode locations (hardly ever more than three with one or two being adequate for most applications) to repeatedly sample essentially the complete myoelectric signal produced voluntarily or involuntarily by the amputee during a time period (a fraction of a second) which is short enough that the signal remains quasi-stationary, comparing from as few as three up to eight or so characteristics of this signal with a range of values these same characteristics were found to encompass in previous tests performed on the amputee, and initiating actuation of one or more functions of the prosthesis when only when the current data on these characteristics all falls within a preselected domain based upon the historical data. Now, to implement such a method, careful consideration must be given to the equipment. The first step is, of course, to obtain accurate measurements of the EMG potentials and this requires a set of electrodes and a high gain differential amplifier.

Commercially available skin electrodes are highly conductive metal electrodes which sometimes require a conducting jelly or other electrolyte to bridge the interface between the electrode and the skin. To further reduce the interface resistance the skin on which the electrodes are to be placed should be washed and then roughened as this will insure minimum interface resistance and thus reduce the pick-up of noise in the surrounding environment. The signal sensed by these electrodes will be a summation of EMG signals, neural signals, cell activity and external noise, chiefly 60 cycle power line interference; however, the EMG signal will be the strongest signal present if the proper application of the electrodes is achieved.

In controlling an upper arm prosthesis, for example, two sets of electrodes are used, one set placed on the biceps and the other set placed on the triceps. Each set of electrodes is composed of two, or at most, three separate electrodes. The leads of the electrodes are connected to a high gain differential amplifier in which the center electrode is used as a reference point and the electrodes on either side are used as the differential input. In such an arrangement the electrical difference between the two input electrodes is amplified. This arrangement has been chosen since outside disturbance, such as 60 cycle interference which is present at both input electrodes, is not amplified due to the high common mode rejection ratio of the amplifier. To help eliminate the 60 cycle interference even further, a cylindrical piece of wire gauze shielding can be used to surround the leads connecting the electrodes to the amplifier. Frequencies above 1.5 K Hz and below 1.5 Hz are preferably filtered out to preserve the dominant EMG signal frequencies from contamination from other sources.

Once a good measurement was obtained of the EMG signal for the various function of interest, this analog measurement was converted to a digital signal which is suitable for analysis on a Intellec 8 Mod. 80 microcomputer. The machine, referred to as an "analog to digital converter" that performs this conversion is essentially a 10-bit analog to digital recorder which can be sampled at a total rate of 25 K Hz to 5 K Hz. After analog to digital conversion is complete, the digital representation is outputted to the aforementioned microcomputer. Since the Intellec 8 Mod. 80 is an 8-bit machine, in order to achieve adequate accuracy of identification and function discrimination, all algorithms of the aforementioned microcomputer were run in double precision. Finally, because this microcomputer is somewhat slow in carrying out multiplication and division operations, Fairchild hardward multipliers and dividers were used and interfaced with it to perform all multiplications and divisions.

In a practical EMG controlled prosthesis the limiting element in the prosthesis will be the speed and accuracy of the on-patient computer that will be necessary for the analysis that is required. The total time between the initial taking of data and final actuation must not take more than approximately 0.2 seconds for a smooth, natural prosthesis control, therefore, algorithms used on the microcomputer for parameter identification and function determination should not use operations more complex than multiplication, division, subtraction and addition. These are the basic operations that can be performed easily and quickly by any microcomputer. A third order AR model using a recursive least-squares algorithm uses 36 multiplies, 30 additions, six subtractions and one divide in each iteration of the algorithm and thus satisfies this criteria. Any function recognition algorithm must also use these basic operations and separate the functions adequately for reliable prosthesis control.

The first step in any function recognition program is to build up a reference parameter domain for all the desired functions. All current or instantaneous parameters will then be compared to this preselected reference parameter domain to determine which function it belongs to. Once its functional origin is determined then the prosthesis may be actuated in accordance therewith. To build up this reference parameter domain the patient will be asked to perform a sequence of predetermined muscle contractions which would correspond to rest, elbow bending, elbow extension, wrist pronation, wrist supination, grasp closed and grasp open. While each function is being performed a set of three to up to eight AR parameters of a suitable model order will be taken from two electrode locations, say the biceps and triceps. For the seven functions of hold (the "hold" mode is employed if no other function has been recognized and it implies that the previously-recognized function is kept), elbow bent, elbow extended, grasp closed, grasp open, wrist pronate and wrist supinate, the total time to create a reference domain would require less than a minute. The determination of this reference parameter domain calibration could be done once a year or once a day, depending on how stationary the parameters are. Applicant has found that calibration is seldom required oftener than once a week and, perhaps, even less frequently even with amputees who have had no previous EMG training of their muscles. Once this parameter domain is obtained the function recognition algorithm employed to determine subsequent parameter identity is limited only by computation time and accuracy.

The relatively complex upper arm prosthetic appliances may require two sets of electrodes and two microcomputers connected in parallel with one another if the analysis of the signal is to be completed in a reasonable period of time using the currently-available microprocessors and if all seven of the previously-listed elbow, wrist and hand functions are to be performed thereby because not all of the seven functions can, as yet, be discriminated via a sinngle set of two or three electrodes. As many as four sets of electrodes and a corresponding number of microcomputers could, of course, be used on a bi-lateral above-elbow amputee (two for each arm) and still stay within the practical constraints of weight and size with which the amputee must function; however, there are few applications where more functions will need to be controlled than are available in accordance with the teaching of the instant invention from AR parameters taken from just two sets of surface electrodes. The parallel computer systems cooperate with one another to identify the AR coefficients of the tricep and bicep muscles, whereupon, this current information is compared with preselected standards based upon historical information on the same parameters to decide whether a given function or functions is to be initiated. Once the "match" between the current data and the stored standard has been made, it becomes a simple matter to initiate one or more outputs capable of actuating the prosthesis in the desired mode or modes through the medium of well-known motor-controllers which form no part of the instant invention.

In processing the signals from the point at which they are picked up by one or more sets of electrodes until the several AR parameters derived therefrom are converted into function-initiating outputs, a good deal happens which perhaps, deserves at least some explanation. Fortunately, recent advances in computer technology have resulted in the creation of microprocessors which are in fact micro central processing units (CPU). The introduction of microprocessors makes it possible to attempt the rigorous analysis of EMG signals for prosthesis control of the type which has already been described. The microprocessor and associated peripheral hardware can be built to almost any size specification but a 4 × 4 × 2 inch unit is easily built and yet it still satisifes reasonable cost considerations. Representative basic components of this system have been found to be a Datel Systems D.C. Instrumentation Amplifier, a Datel Systems DAS-16-L10B data Acquisition System for analog to digital conversion purposes, an Intel 8080 Microprocessor System such as is used in the Intellec 8 Mod. 80 microcomputer referred to previously, and a suitable actuation system of a type well known in the art. The entire prosthesis controller would appear as in FIG. 2, perhaps supplemented by conventional multiplier-dividers for each computer to speed up the processing time.

The electrodes, differential amplifier and data acquisition system of FIG. 2 will be treated as one unit because their combined effect is to insure that the EMG data is properly obtained and made available for input into the microprocessor. The basic consideration is one of timing between the microprocessor and the data sampling system. The timing between the two systems is critical because the microprocessor must be ready to accept data from the data sampling system at the rate of 5000 16-bit words a second.

The microprocessor of FIG. 2 will be discussed separately. It is the brain of the entire system and controls the interaction of all the units of the prosthesis controller. Its main duties are storing EMG data, analyzing the data to determine its functional origin, and the outputting of the proper control commands to control the prosthesis as well as the different components of the prosthesis controller.

The last unit of the controller is the actuation mechanism. Its duty is to take the output control command and actuate the correct motor element of the prosthesis, and to insure correct electrical operating conditions for the prosthesis driving elements, all of these functions being those that are well within the skill of an ordinary artisan having access to the prior art actuating mechanisms.

The Datel Systems Data Acquisition System (DAS) is the main component of the data sampling system. Its volume is only 34 cubic inches (1.5 × 4.5 × 5.0 inches) and its power consumption is less than 7 watts. The DAS was designed primarily to interface with most mini and microcomputers available on the market today and can be easily interfaced to the Intel 8080 microcomputer. There are four modules that are combined to form this system. These modules are an 8 channel analog multiplexer module (MM-8), a sample and hold module (SHM-1), an analog to digital converter module (ADC-L) and a system control logic module (SCL-1).

The MM-8 module is described in detail in Datel Systems Bulletin MM8AT15310. It consists basically of 8 MOS-FET Switches with a four-bit decoder address which selects each switch individually. Thus, one is able to choose any of the 8 inputs to suit his needs. The output of the MM-8 goes to the input of the SHM-1 circuit which samples the output of the multiplexer at a specified time and then holds that voltage level at its output until the analog to digital converter performs its conversion operation.

The SHM-1 module is described in detail in Datel Systems Bulletin SH1BT15310. This module consists of a high input impedance amplifier coupled by a FET switch into the holding capacitor at the input of a low impedance output amplifier. Its chief function is to decrease the aperture time of the system from the total analog to digital converter time down to less than 50 ns. The output of the sample and hold circuit is inputted into the analog to digital converter (ADC). The ADC, when commanded to begin conversion, will take the analog voltage present at its input and through a process called "quantization" will convert this analog signal into a set of discrete output levels. The quantization level or bit size for a ADC of N-bit resolution will be: |maximum analog voltage range permissible|$/2^N$. A 10-bit ADC will have $2^{10}$ discrete output levels. The discrete output levels can then be represented by a set of numbers such as a binary code. The ADC-L uses a quantization process called the "successive approximation technique". This type of technique is generally used for high speed sampling operations.

The interaction between the MM-8, SHM-1 and the ADC-L is all controlld by the system control logic module (SCL-1). The SCL-1 is a control module, the basic task of which is to provide proper sequencing signals for operation of a complete data acquisition system. Interaction between the DAS and other peripheral equipment (analog input devices or microprocessor) is achieved by properly timed inputs to the control lines of the SCL, more detailed information on which can be found in Datel Systems' Bulletin MAQADH5401. The control over the entire system is provided by the microprocessor in conjunction with suitable control logic to achieve the desired interaction.

The microcomputer used in this prosthesis is an Intellec 8/Mod 80. This microcomputer has a complete eight-bit parallel central processing unit (CPU) called the Intel 8080 microprocessor. It is fabricated on a single LSI chip using the latest advances in N-channel silicon gate process and is furnished in a 40 pin dual in-line ceramic package. This process accounts for the high performance of this microprocessor which results in a basic machine cycle of 2 microseconds for instructions that do not reference memory during their execution. A complete microcomputer system results when the 8080 microprocessor is interfaced with up to 256 input and output ports (I/O ports) and with up to 64 K bytes of semiconductor memory. This resulting computer is ideal for high performance solutions to control applications and processing applications that are required on eight-bit binary instruction/data formats.

The Intel 8080 CPU has a set of 78 basic instructions with provisions for arithmatic and logic operations, register to register and register to memory transfers, subroutine handling, I/O transactions and decimal arithmetic. Four internal status flags enable the user to program conditional branches based on carry, sign, zero and parity, Six eight-bit scratch pad or index registers labeled B, C, D, E, H and L are provided for fast data manipulation between memory accesses. The H and L registers are designed to double as a memory address pointer during the execution of memory reference instructions. The combined 16-bit content of the H and L register specifies the memory address location to be accessed. A 16-bit program counter is used to store the address of the current instruction being executed. This allows the CPU to address instructions stored in any portion of memory. A stack pointer was created for the 8080 CPU to allow it to store the contents of the scratch pad registers, accumulator and the status bits of the arithmatic logic unit (ALU) or the program counter. This will permit any portion of memory specified by the 16-bit address contained in the stack pointer to be used as a push down stack. Thus, the stack pointer feature permits the almost unlimited nesting of subroutines or multilevel interrupts. Finally, the built-in control logic for the processing of holds and interrupts, and a synchronization provision for slow memory devices round out the CPU's capabilities. It is this last feature, the built-in control logic, that allows one to easily interface to peripheral devices (DAS, memory and other computers) to the Intel microprocessor to build a computer or computer controlled system.

The 8080 CPU consists of four functional blocks, namely:

1. Register array and address logic
2. Arithmetic and logic unit
3. Instruction register and control section
4. Bidirectional, tri-state data bus buffer The register section of interest to the user is a static ram (random access memory) array organized into five 16-bit registers which are the program counter (PC), the stack pointer (SP), and six eight-bit general purpose index registers referred to as B, C, D, E, H and L. The program counter contains the memory address of the current instruction and is incremented automatically during every instruction fetch cycle. The stack pointer maintains the address of the next available location in memory to be used as a first in last out stack. The stack pointer's address can be initialized by a "LXI SP" instruction to use any portion of the random access memory as a stack. The stack pointer is decremented or incremented automatically depending on whether data has to be stored in or taken from the stack. The six general purpose registers can be operated on by instructions as either single registers (eight-bit) or as register pairs (16-bit). When used as register pairs, the three pairs are denoted as BC, DE and HL. When used in pairs, it is possible to use these paired registers as address locations whenever the "LDAX" instruction is used. Normally the address logic of the CPU uses the H and L registers for memory addressing.

The arithmatic and logic unit contains an eight-bit accumulator register (ACC), and eight-bit temporary accumulator register (ACT), a five-bit flag register and an eight-bit temporary register (TMP). The arithmatic, logical and rotate instruction affect the operation of the ALU. The TMP and ACT are involved in the internal workings of the ALU and are not stored in the ACC and the status register. The ACC is similar to any of the single scratch pad registers but its contents are changed when the ALU is operated. The status register provides information on five status flip-flops that are affected by ALU operation. The status bits are carry, zero, sign, parity and auxiliary carry. The carry bit when set, indicates an overflow or underflow. The zero bit indictes that the result is zero. The sign bit signifies when the MSB of the result is 1. The parity bit indicates when the parity of the result is even. The auxiliary carry bit indicates a carry in decimal instruction operations. Some, but not all, of the status bits are affected during ALU operation depending on which instruction is being performed.

The 78 executible instructions of the 8080 microprocessor are classified as one, two, or three byte instructions. These instructions are incorporated into programs much like the more familiar Fortran programming language. The 8080 microprocessor language is a much lower level language the Fortran. Any arithmatic functions higher than addition or subtraction may be created in a software program by the user or supplied by a suitable hardware peripheral. After a program has been written, it is converted from its mnemonic form to an eight-bit binary number and is loaded into a user defined portion of memory. Each mnemonic instruction has its own distinct binary code. This conversion from mnemonic instruction to binary code can be done by hand or by the software and hardware programs provided by Intel. Once the instructions of a program and in memory these instructions can be fetched from memory by the normal operating procedure of the microprocessor.

During the instruction fetch the first byte of an instruction is transferred from memory to the eight-bit instruction register by an internal bus. The contents of the instruction register are then made available to the instruction decoder. One byte instruction will be executed, but two or three byte instructions will fetch the remaining bytes of the instruction before execution will be completed. The remaining bytes of these instructions are treated either as data or memory address. The output of the instruction decoder is also combined with various timing signals to provide control signals for the memory, ALU, data buffer blocks, and peripheral equipment. In addition, the outputs from the instruction decoder and external control signals feed the timing and state control section which generate the state and cycle timing signals.

The eight-bit bidirectional, and tri-state data bus buffers are used to isolate the CPU's internal bus from the external data bus ($D_0$ through $D_7$). This serves to protect the CPU during inputting and outputting of data from possible electrical damage.

The microcomputer control system of FIG. 2 is composed of two Intellec 8/Mod 80 microcomputers, a Datel System DAS 16-L10B data acquisition system, and various latches, decoders, multiplexers, flip-flops and associated logic. The DAS uses two analog inputs. One analog input is from the biceps electrode and the other input is from the triceps electrode. These lines cause the DAS to alternate between two analog inputs at a rate set by the clock frequency applied to the convert control line. Each time the convert line receives a positive pulse it causes the current analog input to be sampled and then switches to the alternate channel. If a 10 K Hz clock signal is applied to the convert control line, then each input channel is sampled at a 5 K Hz sampling rate. When one channel has been sampled and the DAS has converted the analog voltage to its digital representation then an end of conversion (EOC) signal will be generated. The EOC signal and the sequencer outputs are used to signal one of the two computers that data is ready at the DAS output to be stored into memory. The sequencer output indicates which channel has been most recently sampled and thus can be used to insure that the correct sample of data is being sent to the correct computer.

Each interrupt that the computer receives causes the computer to go to an interrupt service routine that is in memory. Through control logic 1 can cause the computer to recognize interrupts from different peripheral devices and thus can respond to each interrupt with a different interrupt service program. Thus, one may define a data sampling mode, a recalibration mode, a teletype output mode, an inter-computer data transfer mode, and any other mode that is needed by allowing each mode to generate an interrupt that, through the control logic, causes a different interrupt service program to be utilized. The teletype output mode is not needed for control of the prosthesis; however, its availability is convenient for testing purposes.

A first interrupt, for example, causes a computer to input data from one of the input ports into memory. The 10-bits of data outputted from the DAS must be broken up into two eight-bit bytes. This is accomplished by a two channel, eight-bit multiplexer and control commands outputted by the interrupt service routine to one of the output ports. A second interrupt is used to allow the two computers to communicate with one another when the function recognition program is being executed. The service routine for this second interrupt controls the output and input of data on another of the input and output ports. A third interrupt is used to recalibrate The AR parameters used in the function recognition program. A fourth interrupt will be generated by a switch operated by the amputee. When the switch is first actuated the computer will switch to the recalibrate mode and then will interact with the patient. The patient will go through a prescribed set of muscle contractions for a predetermined amount of time. Seven different muscle contractions will be required, one contraction for each function for a limb with three degrees of freedom. Each contraction will be held for a period not in excess of 5 seconds. During this time data will be taken and analyzed to set up the reference points for the function recognition algorithm. This recalibration can be done on a regularly scheduled basis or whenever the patient thinks it is necessary. A fifth interrupt will be used if output to a teletype unit is needed. This service routine will set a particular eight-bit code in memory which will determine if output to a teletype is desired. Since a teletype output is not needed other than for testing, the fifth interrupt can be eliminated along with the two I/O ports it requires. Finally, there will be a sixth interrupt. It is needed to enable the start of the prosthetic computer program after the power has been turned on. This is necessary because in an Intellec computer two of the I/O ports are shared with the PROM programmer. If this sixth interrupt is not generated after power is applied to the prosthesis, them limb actuation is not possible.

Actuation of the prosthesis is achived by control commands output to one of the output ports of computer one. Of these eight bits delivered to the output port, three are used to control the prosthesis. A fourth bit is used as a data request line which tells the DAS to start taking data. Both computers must be ready to receive data and only upon the receipt of a data request from both computers will the DAS begin operation. When the DAS begins operation the control logic will automatically generate the first interrupts for both computers to insure proper transmission of data to the appropriate computer. When enough data has been collected, another positive pulse will be generated on the data request line. This will disable the DAS, prevent the generation of the first interrupt and start the analysis of the acquired data. After the EMG data has been analyzed, the resulting AR coefficients will be compared to the set of reference AR coefficients for each function. The computers will the consult with each other by using the second interrupt and decide on the identity of the function. Computer one will then actuate the prosthesis and request more data. This cycle will be repeated continuously until a recalibration interrupt, a teletype output interrupt or a restart interrupt is received.

The interrupts can only be serviced one at a time, therefore, the control circuit was designed such that the first interrupt received will inhibit the effect of the other interrupts until it has been serviced. Thus, the computer is a single level interrupt machine. Once an interrupt is initiated it chooses its appropriate eight-bit restart command (RST) which is placed on the data bus. The computer will then execute this RST command. The RST command tells the computer where the appropriate service routine is located in memory. After servicing the interrupt, the computer will then return to the portion of the main program it was executing before it was interrupted.

It is not possible to externally interrupt the main program. Before any interrupt will be acknowledged by the computer an "EI" instruction (Enable Interrupt) must have been executed. The EI instruction activates the interrupt receiving control line of the computer. If this instruction is not executed prior to the receipt of the first interrupt INT A through the fifth interrupt, then enabling the interrupt line will be ineffectual. The programmer can use this fact to control the introduction or external information into his program.

What is claimed is:

1. For use in combination with an electrically-operated prosthetic appliance for replacing a missing limb, a control circuit responsive to input signals supplied thereto for operating said appliance and a set of at least two electrodes adapted to receive electromyographic (EMG) signals from the stump of the missing limb when fastened thereto, the subcombination for processing said EMG signal preparatory to delivering same to said control circuit which comprises: data processing means for analyzing the EMG signal so as to reduce it to a near minimum number of linear time series model parameters which are effective to differentiate each of several functions of the missing limb from all other functions thereof, data acquisition means for collecting and storing historical data produced by the amputee at the electrodes relative to the maximum and minimum values of said linear time series model parameters for each limb function to be performed by the prosthesis, comparison measuring means for repeatedly sampling current data on said linear times series model parameters produced by the amputee at the electrodes and comparing said current data with a set of predetermined values therefor chosen on the basis of said historical data, and means responsive to the comparison measuring means operative during each sampling interval to deliver one or more output signals to the control circuit effective to initiate or continue actuation of only that function or those functions of the prosthesis wherein the sampled data falls within the set of unique values chosen for a particular function.

2. The subsombination as set forth in claim 1 wherein the linear time series parameters are parameters of an autoregressive (AR) model of an order no longer than eight.

3. The subcombination as set forth in claim 1 wherein the linear time series parameters are parameters of a near minimum autoregressive moving average (ARMA) model.

4. The subcombination as set forth in claim 1 for use in combination with at least two sets of electrodes placed at different locations wherein the data acquisition means includes sorting means for storing data on the EMG signal according to the location from which it was received, in which independent data processing means connected in parallel with one another are provided for processing data on the EMG signal from each electrode location, and in which separate comparison measuring means are employed for each data processing means and set of electrodes feeding data thereto.

5. The subcombination as set forth in claim 1 wherein means comprising a filter receives the signals from the electrodes and preprocesses same to eliminate substantially all frequencies outside the range of an EMG signal preparatory to delivering the signal thus filtered to the data processing means.

6. The subcombination as set forth in claim 1 wherein the comparison measuring means repeatedly resamples the EMG signals approximately every 0.2 seconds.

7. The subcombination of claim 1 wherein the number of parameters is not less than three.

8. The subcombination of claim 1 wherein the number of parameters lies between three and approximately eight.

9. The subcombination as set forth in claim 2 wherein the AR model is produced using a near convergent identification algorithm.

10. The subcombination of claim 2 wherein the number of parameters is not less than three.

11. The subcombination of claim 2 wherein the number of parameters lies between three and approximately eight.

12. The subcombination as set forth in claim 3 wherein the ARMA model is produced using a near convergent identification algorithm.

13. The subcombination of claim 5 wherein the filter eliminates all frequencies below approximately 1.5 Hz and above approximately 1.5 Hz Herz.

14. The subcombination as set forth in claim 9 wherein the identification algorithm is of the least squares type.

15. The subcombination as set forth in claim 9 wherein the identification algorithm is of the moving average type.

16. The subcombination as set forth in claim 12 wherein the identification algorithm is of the least squares type.

17. The subcombination as set forth in claim 12 wherein the identification algorithm is of the moving average type.

18. The improved method for controlling the operating of an electrically-powered prosthetic appliance replacing a missing limb which comprises the steps of: picking up electromyographic (EMG) signals from at least one location on the stump of the missing limb, processing the signals thus received so as to reduce same to near minimum number of linear time series model parameters effective to differentiate each of the several functions performed by the missing limb from each other function thereof, collecting historical reference data developed by the amputee relative to maximum and minimum values of said parameters for each function to be performed by the prosthesis, choosing a set of unique values of said parameters for each function to be performed on the basis of the historical data thus collected and storing said unique values, repeatedly sampling current data on said parameters while comparing same with the unique sets of preselected values stored for each function, and initiating or continuing that function or those functions of the prosthesis during the sampling period when and only when the current parameter values fall within one or more of said unique sets of values chosen therefor.

19. The method as set forth in claim 18 in which the signals are processed to reduce them to autoregressive (AR) parameters of an order no longer than eight.

20. The method as set forth in claim 18 in which the EMG signals are processed to reduce them to a near minimum number of autoregressive moving average (ARMA) parameters.

21. The method as set forth in claim 18 in which the current data on the identified parameters is repeatedly sampled over a period not to exceed that during which a linear time series model of the EMG signal remains substantially stationary.

22. The method as set forth in claim 18 in which the current data on the identified parameters is repeatedly sampled over a period of approximately 0.2 seconds.

23. The method as set forth in claim 18 in which: the EMG signals are picked up from at least two separate locations on the stump, current data and historical data from each electrode location is kept separate from the corresponding data taken from other electrode locations, and data from different electrode locations is used to control different functions of the prosthesis.

24. The method as set forth in claim 18 which includes the step of filtering the incoming EMG signals to eliminate all frequencies outside the normal range thereof.

25. The method as set forth in claim 18 which includes the steps of making an autoregressive (AR) model of the incoming EMG signal and processing same with an identification algorithm which is nearly convergent.

26. The method as set forth in claim 18 which includes the steps of making an autoregressive moving average (ARMA) model of the incoming EMG signal and processing same with an identification algorithm which is nearly convergent.

27. The method as set forth in claim 18 wherein the signals are processed to reduce the number thereof to at least three but no more than eight.

28. The method as set forth in claim 25 in which the identification algorithm is of the least squares type.

29. The method as set forth in claim 25 in which the identication algorithm is of the sequential learning type.

30. The method as set forth in claim 26 in which the identication algorithm is of the least squares type.

31. The method as set forth in claim 26 in which the identification algorithm is of the sequential learning type.

* * * * *